United States Patent [19]

Ducheyne et al.

[11] Patent Number: 4,963,151
[45] Date of Patent: Oct. 16, 1990

[54] REINFORCED BONE CEMENT, METHOD OF PRODUCTION THEREOF AND REINFORCING FIBER BUNDLES THEREFOR

[75] Inventors: Paul Ducheyne, Bryn Mawr; L. D. Timmie Topoleski, Philadelphia; John M. Cuckler, Haverford, all of Pa.

[73] Assignee: Trustees of the University of Pennsylvania, Philadelphia, Pa.

[21] Appl. No.: 291,157

[22] Filed: Dec. 28, 1988

[51] Int. Cl.$^5$ ............................................. A61F 2/28
[52] U.S. Cl. .................................... 623/16; 428/288; 428/293; 428/294; 428/375; 428/378
[58] Field of Search .................... 623/16, 66; 428/288, 428/293, 294, 375, 378

[56] References Cited

U.S. PATENT DOCUMENTS

| | | |
|---|---|---|
| 4,064,566 | 12/1977 | Fletcher et al. |
| 4,239,113 | 12/1980 | Gross et al. |
| 4,365,357 | 12/1982 | Draenert. |
| 4,693,721 | 9/1987 | Ducheyne. |
| 4,718,910 | 1/1988 | Draenert. |
| 4,735,625 | 4/1988 | Davidson. |

FOREIGN PATENT DOCUMENTS

| | | | |
|---|---|---|---|
| 2947839 | 7/1981 | Fed. Rep. of Germany | 623/16 B |
| 2048730 | 3/1987 | Japan | 428/293 |

OTHER PUBLICATIONS

Knoell and Maxwell–"Graphite Fiber Reinforced Bone Cement", 1975 (225–229).
Pilliar and Blackwell, "Carbon Fiber–Reinforced Bone Cement in Orthopedic Surgery" (1976), vol. 10, pp. 893–906.
Pilliar, Bratina and Blackwell–"Mechanical Properties of Carbon Fiber–Reinforced Polymethylmethacrylate for Surgical Implant Applications" (1977), pp. 206–227.
Wagner–"Mechanical Properties of Aramid Fibre–Reinforced Acrylic Bone Cement"–J. Max. Sci. Lettes 14 (1979), pp. 503–506.
Taiisman and Saha–"Tensile Strength of Wire-Reinforced Bone Cement and Twisted Stainless-Steel Wire", vol. 59A, No. 3, Apr. 1977, pp. 419–424.
Fishbane and Pond–"Stainless Steel Fiber Reinforcement of Polymethylmethacrylate", pp. 194–199.
Robinson, et al.–"Mechanical Properties of Poly(-Methyl Methacrylate) Bone Cements", Jour. Biomedical Mat. Res., vol. 15, 203–208 (1981).
Saha and Pal–"Iprovement of Mechanical Properties of Acrylic Bone Cement by Fiber Reinforcement" (1984), pp. 467–478.
Ekstrand et al.–"Carbon/Graphite Fiber Reinforced Poly(Methyl Methacrylate): Properties Under Dry & Wet Conditions", Jour. Biomed. Materials Res., vol. 21, 1065–1080 (1987).
Pourdeyhimi, et al.–"Fracture Toughness of Kevlar 29*/Poly(Methyl Methacrylate) Composite Materials for Surgical Implantations", Annals of Biomed. Engin., vol. 14, pp. 277–294 (1986).
Saha and Pal–"Mechanical Characterization of Commercially Made Carbon-Fiber-Reinforced Polymethylmethacryalte", Jour. Biomed. Mat. Res., vol. 20, 817–826 (1986).
"Carbon–Fiber–Reinforced Polymethylmethacryalte", Jour. Biomed. Mat. Res., vol. 20, 817–826 (1986).
Chapman and Hall–"Fatigue Crack Propagation in Polymethylmethacrylate Bone Cements", Jour. of Mat. Sci., 17 2463–2468 (1982).
Ducheyne et al.,–"Carbon Fiber Reinforcement of Polymeric Materials for Total Joint Arthroplasty", Biomat. & Biomechanics (1983) pp. 67–72.

Primary Examiner—Alan W. Cannon
Attorney, Agent, or Firm—Woodcock Washburn Kurtz Mackiewicz & Norris

[57] ABSTRACT

The distribution of short, fine, reinforcing fibers homogeneously throughout surgical bone cement is accomplished by adding the fibers in the form of bundles of several hundred fibers with the fibers bonded to each other with an adhesive binder that is soluble in the liquid monomer component of the bone cement. The fiber bundles are either premixed with the powdery polymer bead component of the bone cement followed by addition of the liquid monomer or the polymer and liquid are premixed into a viscous liquid and the fiber bundles are gradually added with stirring to the viscous liquid. In either case, as the adhesive binder dissolves in the liquid monomer the individual fibers are freed and continued stirring mixes the fibers homogeneously throughout the cement mass.

29 Claims, 6 Drawing Sheets

Fig. 8
R-PMMA Fracture Toughness

REINFORCED BONE CEMENT, METHOD OF PRODUCTION THEREOF AND REINFORCING FIBER BUNDLES THEREFOR

BACKGROUND OF THE INVENTION

(1) Field of Invention

This invention relates to a fiber reinforced bone cement useful for adhering or grouting bone to the surface of a rigid substrate, such as a prosthesis. More particularly, the invention relates to a fiber reinforced bone cement which can be easily used by a physician during bone repair procedures while providing improved toughness and fatigue strength; to a kit and to a method for preparing the reinforced bone cement; and to a novel fiber bundle for use in preparing the reinforced bone cement.

(2) Problems Solved and Prior Art

In joint surgery it is common practice today to anchor components of replacement joints by using as bone cement a two-component resin which polymerizes during the operation at normal temperatures and which, on account of its plastic properties leads to an interlocking of the prosthesis component in the bony sheath. Because of its physical properties, the bone cement shrinks onto the prosthesis resulting in a closed metal-to-cement contact.

The bone cements commonly used are polymethylmethacrylate (PMMA) consisting of powdery bead polymers which are superficially dissolved by liquid monomers and embedded during the polymerization process. During mixing the polymer is immersed in the monomers. The PMMA beads are superficially dissolved and embedded in a composite manner.

Despite their widespread use PMMA and related bone cements tend to represent the "weak link" in prosthesis fixation.

Figure 1:
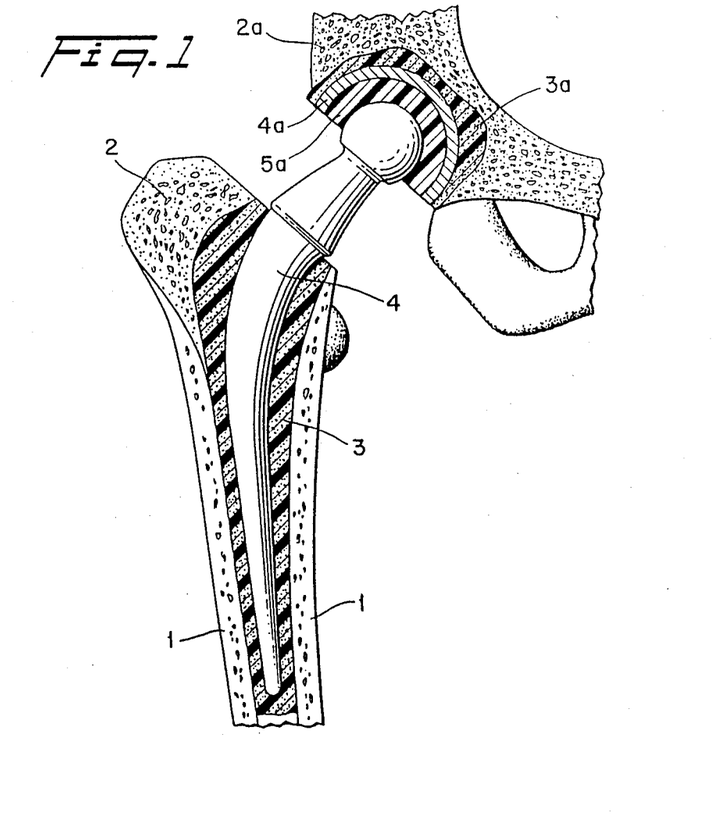
FIG. 1 is a schematic of a total joint prosthesis, showing the relationships of the various materials, both natural (bone) and implanted (metal, cement, etc.)

The long term success of a total joint prosthesis depends on the continued function and interaction of each of the components of the prosthetic system. In a cemented total hip prosthesis, for instance, stress transfer from the pelvis to the femur is a function of the materials between the two bones (e.g. bone-PMMA-metal-UHMWPE[1]-metal-PMMA-bone) and the interfaces between the materials, as illustrated in FIG. 1 for a hip prosthesis (1-cortical bone; 2,2a-spongeous bone, 3,3a-acrylic cement; 4,4a-metal prosthesis; 5a-UHMWPE; where subscript "a" designates acetabular components and the non-subscripted numbers represent the femoral components). The weakest of the materials is the PMMA, with the lowest fracture toughness and ultimate strength.

[1] UHMWPE: Ultra-high Molecular Weight Polyethylene is used as a lubricant material, generally to prevent metal from articulating on metal, and is used, for example, as part of the acetabular component of a total hip prosthesis, or the tibial component of a total knee prosthesis.

The common mode of failure of total joint prostheses is aseptic loosening. X-ray examinations of patients with loosened prostheses often reveal a radiolucent line in the bulk of the cement, indicating that the cement has fractured. Because the geometry of the prosthesis is complex, the state of stress is also highly complex, and the reasons for cement failure are not clear. For example, it has been postulated that the integrity of the metal stem/PMMA interface is the critical link in the performance of the prosthesis; however, the cause and effect relationship between the metal prosthesis/PMMA interface failure and cement fracture is not well understood although the fracture mechanics of the two phenomena are most likely linked. The improvement of the fracture characteristics of the bone cement, however, is a problem that has received some attention in recent years.

The composition of the PMMA used for total joint surgeries today is substantially the same as that used 20 years ago; very little has been done to improve the material itself. The acceptable success rate of cemented prostheses was achieved using existing cements, however, in a predominantly elderly patient population and with improved surgical handling techniques. The 90% success rate at ten years is good, but should be improved. Cement failures do occur, and generally lead to revision surgery. Furthermore, younger patients now receiving total joint replacements have a greater life expectancy than the design expectations of the total joint prosthesis. Improvement of the bone cement, exclusively, may not solve every problem associated with total joint replacements. But, by making improvements in each component of a total joint prosthesis, including the cement, the success rate of prostheses will improve, and mechanical failures can be virtually eliminated.

Increasing the longevity of PMMA by improving the resistance to failure of the polymer has received some, albeit surprisingly little, attention in the bioengineering literature in the past ten years. One suggested method of improvement was to formulate a new bone cement, based on n-butyl methacrylate, rather than the methyl methacrylate monomer. It has been reported that the material showed a higher ductility, a higher apparent fracture toughness, and a greater fatigue life. However, the actual fracture toughness determined by separate impact tests showed no improvement of the new cement with respect to PMMA cements. An even more detrimental result was that the new polymer had only half the modulus and half the ultimate tensile strength of PMMA.

Another method of attempting to improve PMMA was the addition of a reinforcing phase, generally short fibers or whiskers. Early work was done by Knoell, et al., *Ann. Biomed. Eng.*, 3, 1975, pp. 225-229 with carbon fibers approximately 6 mm in length, 1, 2, 3 and 10% fiber content by weight (approximately 0.67, 1.33, 1.96 and 5.87% fiber content by volume, with measured increases of 100% in the average Young's modulus for the reinforced PMMA. They also reported a decrease in peak curing temperature of the reinforced PMMA. They found the reinforced cement viscous and difficult to mix, and they altered the ratio of powder polymer to liquid monomer to facilitate mixing of the reinforced cement. Pilliar, et al., *J. Biomed. Mater. Res.*, Vol 10, 1976, pp. 893-906); *Fatigue of Filamentary Component Materials ASTM STP* 636, eds. Reifsnider, et al., ASTM 1977, pp. 206-227; used carbon fibers (6 mm length, 7 micrometers diameter) with a 2% volume content. They measured a 50% improvement in tension-tension fatigue limit, improved impact performance, and a 36% increase in ultimate tensile strength. However, it was implied that the reinforced PMMA had poor intrusion characteristics due to increased viscosity, and poor fiber distribution. Wright, et al., *J. Mater. Sci. Let.*, 14, 1979, pp. 503-505, did preliminary studies using PMMA reinforced with chopped aramid fibers. PMMA reinforced with 5.17% by volume (7% by weight) exhibited a 74% increase in fracture toughness over the plain PMMA. They were not able to produce reinforced PMMA with a fiber content greater than 5% by volume because of mixing and handling difficulties. Beaumont, *J. Mater. Sci.*, 12, 1977, pp. 1845-1852 included glass beads in the PMMA mass and measured a $10^3$ decrease in crack propagation velocity, using 30% volume content of the beads.

Very few investigations involved the use of metal fibers to reinforce PMMA. Taitsman and Saha, *J. Bone Joint Surg.*, Vol 59-A, No. 3, Apr 1977, pp. 419–425, used large diameter (0.5 to 1.0 mm) stainless steel and vitallium wires as a reinforcing phase. They embedded 1, 2 or 3 wires in their PMMA specimens. They reported up to an 80% increase in tensile strength of the PMMA, with three embedded vitallium wires, but noted that clinical applications of their wire reinforced cement were limited. Taitsman and Saha's use of reinforcing wires is analogous to reinforcing bars embedded in structural concrete, and not a homogeneous, fiber composite material. Fishbane and Pond, *Clin. Orthop.*, No. 128, 1977, pp. 194–199, reinforced industrial grade PMMA and PMMA bone cement with stainless steel whiskers (0.5–1.0 mm length and 65 micron diameter; 3–6 mm length and 90 microns diameter). They determined that the addition of fibers up to 6.5% by volume improved the compressive strength by nearly 100% for the industrial PMMA, but only 25% for the surgical grade PMMA. The compressive strength of PMMA is not a critical property for the longevity of the cement in vivo. These authors postulate that the reason for the decreased performance of the surgical PMMA was: ". . . due to the limitations imposed by the (surgical) methacrylate preparation technique."

Schnur and Lee, *J. Biomed. Mater. Res.*, Vol. 17, 1983, pp. 973–991, used titanium (Ti) sheet, wire, mesh and powder as a reinforcing phase with the purpose of increasing the modulus of PMMA to the modulus of cortical bone. A 16% volume fraction of 1 mm diameter wires (a total of 25 wires) increased the modulus of the PMMA by 380%, and the maximum compressive stress by 75%. The concept is again similar to the reinforcing bars embedded in concrete.

The more recent work in reinforcing PMMA bone cement as reported in the literature, has involved either carbon, graphite or aramid fibers. Robinson, et al., *J. Biomed. Mater. Res.*, Vol. 15, 1981, pp. 203–205, tested both regular PMMA and low viscosity PMMA cement (available from Zimmer Co., Warsaw, Ind.) reinforced with 2% volume of carbon fibers (1.5 mm in length, 10 microns diameter). Both reinforced cements exhibited an increase in apparent fracture toughness (notched bending strength tests) of approximately 32% over their plain counterparts. Surface fractography revealed no evidence of fiber fracture, indicating that the increases in "toughness" was due principally to fiber pull out. In other work with carbon fiber reinforced PMMA an order of magnitude decrease in crack propagation velocity was attributed to the carbon fiber reinforcement of both the regular and low viscosity cements.

Saha and Pal, *J. Biomechanics*, Vol. 17, No. 7, 1984, pp. 467–478, tested PMMA reinforced with carbon fibers, 0.67% by volume (1% by weight; 6 mm length, 8 microns diameter) and PMMA reinforced with aramid fibers (Dupont Kevlar-29), 1.61 and 3.82% by volume (2 and 4% by weight; 12–13 mm length, unspecified diameter). The reinforced PMMA showed an increase in the ultimate compressive strength of 20.5% for the carbon fibers, and 19.5% and 28.7% for the 1.61 and 3.82% volume % aramid fibers, respectively. Two important consequences of the addition of fibers to PMMA were proposed: The peak temperature of the reinforced PMMA was lower than the plain PMMA, and the addition of fibers changed the workability of the cement. They recognized that uniform dispersion of fibers was not achieved. Saha and Pal studied a machine mixing technique for distributing the fibers. Their claim that machine mixed specimens were stronger than non-machine mixed specimens is misleading. They used a different shaped fiber for their machine mixed specimens. It is the superior shape of the fiber which is presumed to account for the increase in strength. Machine mixing was never shown to improve the properties of reinforced PMMA.

Ekstrand, *J. Biomed. Mater. Res.*, Vol. 21, 1987, pp. 1065–1080, fabricated carbon fiber reinforced PMMA by using clinically irrelevant, industrial fabrication techniques with fiber content as high as 16.38% by volume (40% by weight).

Recent work by Pourdeyhimi, et al., *Ann. Biomed. Eng.*, 14, 1986, pp. 277–294, studied the effect of the fiber content of the fracture toughness of hand-mixed, reinforced, dental PMMA. They used aramid fibers from 0.82 to 5.17% by volume (1 to 7% by weight), and graphite from 0.67 to 5.87% by volume (1 to 10% by weight). For each type of fiber reinforced cement, the fracture toughness increased with increased fiber content. The aramid fiber specimens showed a greater increase than the carbon fiber specimens of the same weight percent, presumably because the energy dissipated in the micromechanisms of failure is greater for the aramid fibers than for the carbon fibers. They were not able to produce a uniform distribution of the fibers.

U.S. Pat. No. 4,064,566 to Fletcher, et al. discloses a graphite fiber reinforced bone cement of the acrylic type stated to have mechanical properties more nearly matched to those of bone and thermal curing characteristics resulting in a lower exothermic temperature reaction during curing. The bone cement composition is a dispersion of from 2 to 12% by weight of very fine high modulus graphite fibers having a diameter below 50 microns and between 0.1 to 15 mm in average length in a solution of biocompatible polymer dissolved in a reactive monomer. Fletcher reports only an increase in the modulus of the bone cement, which is not of primary concern to a reinforced bone cement, and indeed can be detrimental to the prosthesis system. There was a decrease in compressive strength, and more negatively, a decrease in flexural strength for the reported composite.

U.S. Pat. No. 4,239,113 to Gross, et al. discloses an acrylic based bone cement filled with between 15 and 75% by weight of inorganic material comprised of about 90 to 99% by weight of a bio-active glass ceramic powder and about 1 to 10% by weight of vitreous mineral, e.g. glass, fibers having a length below about 20 mm. The particle size of the powder is from 10 to 200 micrometers. Fiber diameters are not disclosed. Improvements in impact strength, and compression strength were reported. However, a significant decrease in the bending strength and an increase in the modulus of elasticity were also reported. Further, there are no examples given as to the clinical usefulness of this cement. Bioactive glass degrades with time, and hence the integrity of the reinforced bone cement will also degrade with time. The controlled experimentation shows that there is no mechanical improvement due to the fiber reinforcing phase alone. Any improvement is due to the combination of Bioactive glass and fiber in concert. Since the Bioactive glass degrades with time, the properties of the reinforced cement proposed by Gross, et al. will also degrade with time.

Davidson, in U.S. Pat. No. 4,735,625, reports the invention of a reinforced bone cement formed using a sock-like mesh of a fiber-like material to reinforce the cement in the vicinity of the prosthesis. The volume of "reinforced" bone cement is limited; critical areas are not reinforced. Draenert, in U.S. Pat. No. 4,365,357, presents an invention similar to Davidson's, but using a mesh of polymeric fibers. The invention is restricted to use in repairing bone defects, and not as a bone cement in the sense described for total joint arthroplasty. Draenert, in U.S. Pat. No. 4,718,910, describes a bone cement mixture where a second phase of fibers is added. The fibers, however, are made up of the same polymeric material as the bone cement. Draenert includes a graph of the performance of the new material versus existing cements. The inventor states that the fiber is only effective because of the shape of the prepolymer powder. Therefore, the improvement is due to the use of a different cement, and not to the addition of the fibers.

The use of ductile, high strength, larger diameter, fibers to reinforce the brittle matrix material, PMMA, has certain advantages over reinforcement with brittle fibers, such as carbon or Kevlar. Cooper and Piggott in *Advances in Research on the Strength and Fracture of Materials*, ed. Toplin, Pergammon Press, 1978, pp. 557–601, showed that fracture properties of composite materials improve as the diameter of the fibers increase. However, high strength ceramic fibers, including carbon fibers, are difficult and expensive to produce with diameters greater than 10 micrometers. Ductile fibers also increase the amount of energy dissipated during crack growth, especially in short fiber composites. The use of carbon fibers, therefore, limits the extent to which the mechanical properties of PMMA can be improved.

With this background in mind, the present inventors have been engaged in an extensive research program designed to study the mode of failure of surgical bone cements based on acrylic polymers and means for improving the fracture toughness, tensile strength, modulus, and other physico-mechanical properties, while taking into consideration the requirement that the surgical bone cements must be easily mixed by the surgeon under clinical conditions (e.g. in the operating room) and must remain workable for sufficient periods of time to be applied without extensive use of force.

As a result of this research it became apparent that the use of short metal fibers as reinforcement for acrylic based surgical bone cements would offer the most significant improvements in the strength characteristics. The short metal fibers provide the following advantages when used to reinforce the acrylic based surgical bone cement: the fibers are ductile and still provide fracture energy dissipation mechanisms that are not available for other types of reinforcing fibers, including carbon or graphite, glass or ceramic, or polymeric reinforcing fibers; the diameters of the metal fibers can be widely varied by altering the drawing conditions during the manufacturing process; metal fibers have generally high strength and high fracture toughness.

It is generally agreed that as the quantity of reinforcing fibers increases so do the mechanical strength properties. However, as the fiber content increases it becomes increasingly difficult and eventually not practical or possible to effect homogeneous distribution of the fibers throughout the cement mass and in addition the viscosity of the mass increases and its workability by the surgeon during surgery decreases. Any practically useful surgical bone cement must be capable of being easily mixed by the surgeon in a clinical setting, i.e. during surgery, and must remain sufficiently flowable and workable to be applied to the bone surface or cavity and/or to the prosthesis or other implant device.

SUMMARY OF INVENTION AND OBJECTS

Accordingly, it is an object of the invention to provide a surgical bone cement with improved mechanical properties, including fracture toughness and fatigue strength, thereby improving long term prognosis of total joint replacements and other surgical bone repair treatments involving bone cements.

It is another object of the invention to provide a fiber reinforced surgical bone cement wherein mixing of the fiber reinforcement into the cement matrix can be easily performed by the surgeon under clinical conditions.

Still other objects of the invention are to provide a novel fiber reinforcing material which can be easily and homogeneously incorporated into a two component bone cement including biocompatible polymer beads or powder and biocompatible reactive liquid monomers; a bone cement treatment kit for surgical bone repair which kit includes the fiber reinforcing material, biocompatible polymer and reactive liquid monomer; and a method for uniformly and homogeneously incorporating short fine fiber reinforcing material into a two component acrylic based surgical bone cement.

The above and other objects of the invention which will become more apparent after reading the following detailed description and preferred embodiments in conjunction with the accompanying drawings are accomplished, according to a first aspect of the invention, by an acrylic based surgical bone cement reinforced with short fine fibers which are randomly but homogeneously distributed throughout the cement matrix, the fibers having an average length of from about 0.5 to 10 millimeters and an average diameter of from about 5 to 100 microns. Preferably the fibers are incorporated in an amount up to about 20% by volume of the cement composition.

In accordance with a further aspect of the invention, a fiber reinforcing material is provided which facilitates its homogeneous incorporation into and throughout the acrylic based bone cement. The fiber reinforcing material is formed as a bundle of short fine fibers bonded together by an adhesive material which is soluble in the liquid monomer component of the acrylic bone cement. Preferably, the fiber bundles have a length-to-diameter ratio in the range of from about 10:1 to 1:10.

The fiber reinforcing material can be provided as a component of a bone cement treatment kit for surgical bone repair or other treatment of a bone disease or bone defect requiring application of a surgical bone cement. The kit includes a biocompatible polymer, generally in the form of powder or beads, a liquid reactive monomer, and a plurality of bundles of reinforcing metal fibers wherein the fibers in each bundle are bonded to each other with an adhesive material which is soluble in the liquid reactive monomer. When the three components are combined with stirring, the adhesive material will dissolve in the liquid monomer to thereby allow and promote the individual fibers of the bundles to be homogeneously distributed throughout the bone cement.

According to another aspect of the invention there is provided a method for preparing a fiber-reinforced bone cement for surgical application. In one embodiment of this aspect, the adhesive-bonded reinforcing fiber bundles are first mixed with the powdery or granular polymer to form a first mixture and then the first mixture is further mixed with the reactive liquid monomer, whereby the adhesive material bonding the individual metal fibers of the fiber bundles dissolves in the liquid monomer to thereby promote homogeneous distribution of the reinforcing fibers throughout the bone cement.

In another and preferred embodiment of this aspect, the powdery polymer and liquid monomer are pre-mixed until a viscous liquid is formed, the fiber bundles are gradually added to the viscous liquid mixture, and the resulting mixture stirred to distribute the fiber bundles throughout the resulting mixture, while allowing the adhesive component to dissolve in the liquid monomer whereby the individual fibers of the fiber bundles are released into and randomly distribute throughout the bone cement.

DETAILED DESCRIPTION OF INVENTION AND PREFERRED EMBODIMENTS

In this invention, the terms "(meth)acrylate" and "poly(meth)acrylate" include the monomers and polymers, respectively, of methacrylic acid esters and acrylic acid esters, and the polymers also include the co-polymers of the compounds named.

The preferred bone cement material to which the fiber reinforcement is added includes a solid finely divided powdery or granular polymer component and a liquid reactive or polymerizable monomer component which is also a solvent or swelling agent for the polymer component. The polymer and monomer components can be based on the acrylic, e.g. (meth)acrylate system, however, other polymeric systems can also be used. For convenience, the cement system may at times be broadly referred to as an acrylic polymer, or as based on PMMA (polymethylmethacrylate), the preferred polymer component.

More generally, the polymer component of the composition can be any methyl(meth)acrylate polymer such as methyl(meth)acrylate homopolymers and copolymers of methyl(meth)acrylate with alpha,beta-ethylenically unsaturated compounds such as vinyl acetate, alkyl (e.g. $C_2-C_6$) (meth)acrylates and multi-functional acrylic monomers such as alkylene dimethacrylate and alkylene diacrylates and triacrylates. These polymers generally have a molecular weight between 500,000 and 2,000,000. Methylmethacrylate homopolymers and copolymers are preferred.

The reactive monomer component is preferably methyl acrylate or methyl methacrylate although the $C_2-C_4$ alkyl(meth)acrylates, such as ethyl(meth)acrylate, propyl(meth)acrylate or (n-, or iso-)butyl (meth)acrylate, can also be used.

These bone cement materials, which are themselves wellknown and commercially available, are usually provided with 2 parts by weight of the finely divided polymer and 1 part by weight of liquid monomer, although higher or lower ratios can also be used, and are characterized as being self-polymerizable substances which are mixed, together with a polymerization catalyst, such as dibenzoyl peroxide, and polymerization accelerator, such as dimethyl-p-toluidine, immediately prior to the operation to form a viscous liquid or pasty mass. The pasty mass is introduced into the appropriate body cavity and/or to the surgical implant device, and will harden in situ, at room temperature (via an exothermic reaction) within a few minutes.

More specifically, curing of bone cement composition is typically accomplished by any suitable initiator system such as from about 0.1 to about 3% by weight, preferably about 0.6% of a conventional free radical initiator. The initiator can be a peroxy compound or an azo compound. For purposes of biocompatability benzoyl peroxide is a very suitable free radical initiator. The curing temperature is generally reduced to room temperature, e.g. about 25° to 30° CC. by inclusion in the formulation of an activator for the peroxide catalyst which causes more rapid decomposition of the peroxide to form free radicals. Suitable peroxide catalysts include benzoyl peroxide, 2,4-dichlorobenzoyl peroxide and 4-chlorobenzoyl peroxide. Activators or accelerators for these catalysts include N,N-dialkyl anilines or N,N-dialkyl toluidines generally employed in amounts ranging from about 0.1 to 1% based on the weight of monomer present. A preferred activator is N,N-di(2-hydroxyethyl)-p-toluidine. In order to provide longer shelf life for the compositions of the invention, the composition may be stored in a closed container at cold temperature. Stabilizers, such as hydroquinone or chlorophyll may also be added to the monomer compound. Bone cements containing both activator and peroxide are provided as two-part compositions in which the activator and monomer and peroxide and polymer component are packaged in separate containers. The proportions by weight of polymer and liquid monomer can range from about 4:1 to 1:2, preferably 3:1 to 1:1.5, such as 2:1, 1.5:1, 1:1 or1:1.5.

While it is known, as indicated by the literature and patent art discussed above, to incorporate fiber reinforcing material into the bone cement, in actual practice it has proven difficult to incorporate the short, fine fibers, in significant amounts, uniformly and homogeneously throughout the viscous cement mass.

The primary hindrance to a uniform fiber distribution is that the fibers tend to clump together. That is, any given fiber will not move freely when it is surrounded by other fibers, presumably due to friction and other fiber surface effects. The high viscosity of the bone cement, which begins to cure immediately upon mixing the cement components, further exacerbates this problem which is also made more acute by virtue of the practical requirement that the mixing takes place in the operating room by the surgeon (or his or her assistants) where large scale high power mixing equipment is neither available nor appropriate. Usually mixing is accomplished totally manually, e.g. using a bowl and spatula, although small, low power mixers or blender may be available.

The present invention provides a solution to fiber clumping and substantially avoids the resulting fiber distribution problem by allowing the reinforcing fibers to move freely with respect to one another. This is accomplished by providing the fibers in small, discrete bundles with greatly expanded, low aspect ratio. An embodiment of such a fiber bundle, with a rectangular cross-section is shown at 10 in FIG. 3. A cylindrical fiber bundle, i.e. circular cross-section, according to the invention is shown generally at 20 in FIG. 4. The fibers 30 in each bundle are bonded together with an adhesive 50 which is soluble in the liquid monomer component of the bone cement. The resulting fiber bundles or "nuggets" are easy to work with and can be easily distributed throughout the pasty cement mass while still in the liquified (although viscous) state. The bundles effectively reduce the aspect ratio (length/diameter) of the individual fibers in a mass of powder or liquid. High aspect ratio particles (long thin fibers) increase the viscosity of a fluid, while low aspect ratio particles (like the bundles), do not increase the viscosity greatly, but may provide insufficient reinforcement. The low aspect ratio bundles are closer to spherical particles than individual fibers. The bundling process, using a coarse analogy, takes fibers and bundles them into rough spheres. High aspect ratio fibers also tend to tangle and will not disperse uniformly.

As the fiber bundles are stirred into the liquefied cement mass the glue binding the fibers together is dissolved in the liquid monomer component, the bundles start to break up, and the individual fibers of each bundle are distributed randomly throughout the cement mass.

Figure 5:
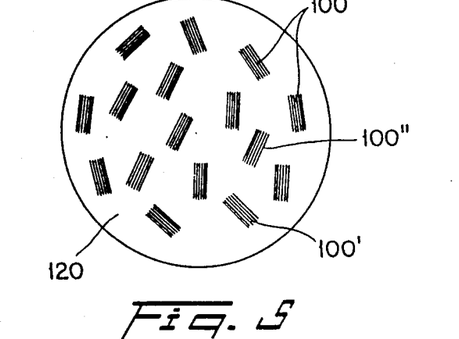
FIG. 5 is a schematic view, in cross-section, according to one embodiment of the invention, showing the distribution of discrete fiber bundles in the viscous liquid cement.
Figure 6:
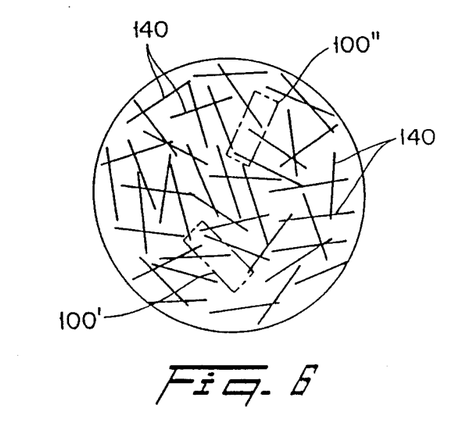
FIG. 6 is an enlarged schematic view, in cross-section, of a portion of the fiber reinforced bone cement of FIG. 5 after the adhesive binder of the bundles has dissolved and the individual fibers are randomly and homogeneously distributed throughout the cement mass.

Thus, in the first instance, and referring to FIG. 5, the use of fiber bundles 100 allows the bundled fibers to be easily distributed throughout the cement mass 120. Secondly, the use of a glue for the fiber bundles which dissolves in the liquid monomer and continued stirring then allows the individual fibers 140, of each bundle, e.g. bundles 100' and 100", to be randomly and homogeneously distributed throughout the bone cement as schematically illustrated in FIG. 6 before it is fully cured.

In the present invention, the reinforcing fibers are preferably formed of ductile, high strength metal materials, rather than the more brittle carbon or ceramic fibers or high strength synthetic fibers, such as the aromatic polyesters or polyamides, e.g. Kevlar ®. However, the advantage of the present invention, in terms of the more homogeneous distribution of the reinforcing fibers throughout the bone cement, etc., can also be achieved with carbon, graphite, ceramic, vitreous, or high-strength synthetic polymeric fiber materials. Mixtures of different types of fibers can also be used.

The use of metal fibers is preferred in view of their high strength, ductility, and ease of manufacture in various diameters using conventional metal fiber drawing technology.

The preferred metal material is titanium although any other biocompatible, ductile, biologically inert and sterilizable metal can be used. Other appropriate metals include, for example, cobalt-chromium alloys, tantalum, niobium, alloys of these metals with each other and other metals, and the like. Titanium is the preferred metal since its biocompatability is well documented. Other metal fibers, such as stainless steel, may also be used for certain applications, but because of the possibility of crevice corrosion the use of stainless steel is not generally recommended.

The size of the reinforcing fibers is important to assure the desired improvements in strength of the reinforced bone cement without an unacceptable decrease in workability of the mixed uncured cement composition resulting from reductions in flowability (i.e. increase in viscosity). In order to have a minimum impact on flowability, the fibers should be as short as possible; viscosity increases with increasing fiber length. However, longer fibers provide increased strength as compared to an equivalent amount of shorter fibers.

Accordingly, fibers having lengths in the range of from about 0.5 to about 10 millimeters, preferably from about 1 to about 8 millimeters, such as 1.5, 2, 3, 4, 5 or 8 millimeters, are used in this invention. Furthermore, within this range, the fiber size should be preferably selected to be accommodated within the anticipated thickness of the cured bone cement, which, depending on the particular patient and type of surgery, etc. may range from only a few millimeters to several or tens of millimeters. As shown by the examples that follow 1.5 mm long metal fibers produce substantially the same degree of fracture toughness results as the 5.0 mm long fibers.

Fiber thickness (diameters) should be selected within the range of from about 5 to about 100 microns, preferably from about 8 to about 80 microns, especially preferably from about 12 to 60 microns, such as 12, 20, 30, 40 or 50 microns. Below about 5 microns the total surface area of the fibers becomes unduly high, leading to excessive adsorption of the liquid monomer, and the strength of the reinforced cement is not sufficiently increased. Above about 100 microns the flexibility of the fibers is somewhat diminished, and there exists the possibility of puncturing surgical gloves in a clinical situation.

Within the above ranges of lengths and diameters fibers having length-to-diameter (l/d) ratios in the range of from about 20:1 to about 1000:1, preferably from about 40:1 to about 600:1, are preferred.

To form the individual fibers into bundles, a large number, e.g. from about 50 to 500, preferably 100 to 300, of the continuous length fibers are gathered together, preferably in longitudinal alignment or substantial alignment, and the resulting fiber array is passed through a supply of binder or glue, according to techniques well known in the art. After the binder has cured or at least set to a stage where it is no longer tacky the bonded fiber array is cut into individual bundles of the desired length.

Typically, the metal fibers will be drawn from rods or wires or bundled wires through a single die orifice, the drawn fibers being stretched and drawn to the predetermined fiber diameter and after drawing the fibers from one or more drawing machines are gathered by a gathering device. Preferably, in order to draw the metal fibers to the desired diameters, particularly diameters of 25 microns or less, it is convenient to start with a bundle of wires, e.g. from about 10 to about 100 or more wires, tightly encased within a metal tube, such that drawing the tube will simultaneously draw the individual fibers, usually through several passes, until the desired diameter is reached. Then, the metal tube is chemically etched away, e.g. dissolved, using an etchant liquid which will not dissolve the metal fibers. The thus freed metal fibers will usually have a hexagonal-like cross-section as a result of the tight packing in the tube. The metal tube may be copper, steel, stainless steel, or other easily drawable metal which can be dissolved, e.g. in an acid bath, which will not dissolve the reinforcing metal fibers This metal fiber drawing technology is well known in the art. Before or after gathering into a fiber package or array the fibers are passed through a supply of adhesive material which will bind or glue together the individual fibers in each fiber package. The adhesive may be in the form of a finely divided powder in which case the powder adhering to the fibers will be caused to melt, either due to the high temperature of the fibers or by external application of heat, and the molten adhesive can flow around and coat the individual fibers as well as into the interior of the fiber package in the case where the fibers are closely packed when they pass through the adhesive powder. Alternatively, the adhesive may be in the liquid or molten form when it comes into contact with the fiber package.

If the adhesive is applied to the fibers before the fibers are gathered together to the final dimension of the bundle the fiber array will then be passed through one or more gathering devices, which may simply be a single aperture or tube or several apertures or tubes of continuously decreasing diameter, with the last aperture having the diameter desired for the fiber bundle. The gatherers may also function as adhesive metering devices to wipe off excessive adhesive as the fiber array passes through and contacts the edge of the aperture. The speed of travel of the fibers through the adhesive supply and through the gatherers will be such that the adhesive is not fully set or cured until after the fiber array passes through the last gatherer. The apertures or tubes through which the fiber packages are gathered may have any desired geometrical shape, but will usually be circular, square or rectangular in cross-section. Similarly, the fiber bundle products may have any desired cross-sectional configuration, such as circular, rectangular, square, etc. Furthermore, even with apertures having circular cross-sections the fiber bundles may generally flatten to a more rectangular cross-section during the curing process.

Figure 3:
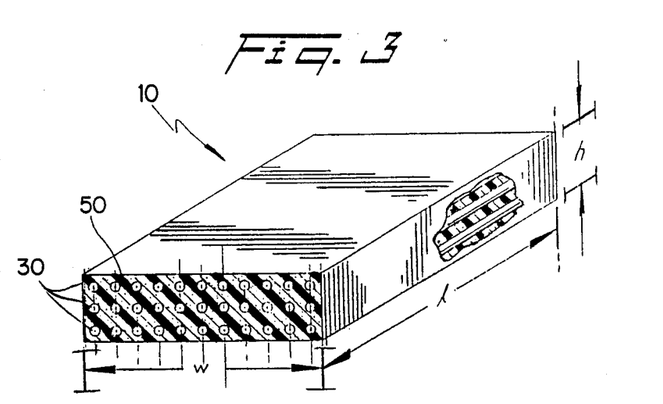
FIG. 3 is a schematic side elevation view, partially broken, of an embodiment of a fiber bundle with a rectangular cross-section according to this invention.
Figure 4:
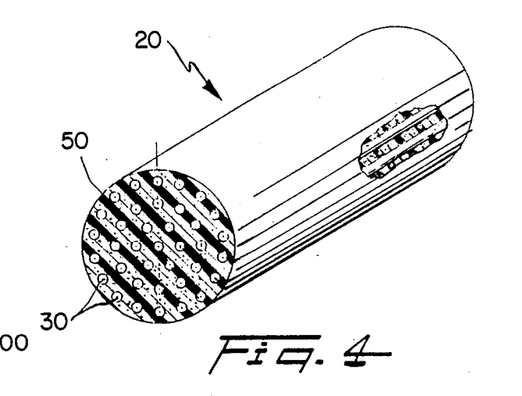
FIG. 4 is a schematic side elevation view, partially broken, of another embodiment of a fiber bundle with a circular cross-section according to the invention.

Furthermore, before or after the adhesive is fully cured, but preferably after the adhesive is no longer tacky to the touch, the fiber array is cut by any appropriate cutting device into fiber bundles. The fiber bundles, depending on the number and diameter of the fibers in the bundle will itself have a diameter in the range of from about 1 to about 10 millimeters, preferably from about 2 to 8 mm. Furthermore, to assure uniform distribution of the fiber bundles in the cement mass with minimum tangling and viscosity increase and for ease of handling, the aspect ratio, i.e. length-to-diameter (l/d) ratios of the fiber bundles will range from about 10:1 to 1:10, preferably 3:1 to 1:3, more preferably 2:1 to 1:2. As used herein "length-to-diameter (l/d) ratios" for fiber bundles which do not have a circular cross-section are determined on the basis of the longest edge dimension of the cross-sectional configuration. For instance, for a fiber bundle of length (1) and with a rectangular cross-section, such as shown in FIG. 3, of width w and height h, where w>h, the aspect ratio (length-to-diameter) ratio is taken as 1/w. This definition is consistent with general principles of bulk viscosity measurements. In short, the contribution to increased viscosity in the bone cement is due to the larger dimension. Since, in the illustrated case of FIG. 3, the height (or depth) h of the fiber bundle is small with respect to the length 1 and width w, the contribution to increase in viscosity (e.g. from the "drag" of the fiber bundle through the cement matrix) will be negligible.

The adhesive binder for the fiber bundles may be selected from any biocompatible material which is soluble in the liquid monomer component of the bone cement. The adhesive material should also be compatible with and not adversely affect the curing or strength of the bone cement.

The preferred adhesive binder materials are selected from the (meth)acrylate compounds, and may be the same as or different from the polymer or liquid monomer component of the bone cement.

Particularly good results are obtained with poly(butylmethacrylate) adhesive compositions and with poly(methylmethacrylate) adhesive compositions.

The amount of the adhesive binder for the fiber bundles is not particularly critical but generally may be the minimum amount required to hold the fibers in the fiber bundles during handling. For example, it is not necessary that all of the fibers are uniformly or even totally covered by the adhesive binder. However, the amount of adhesive binder should also be sufficient to allow the bundles to be distributed throughout the mixed bone cement polymer and monomer before the adhesive is substantially dissolved in the monomer component and a significant proportion of the individual fibers are released from the bundle into the cement mixture. Usually, an amount of adhesive binder ranging from about 1 to about 20% by weight of the metal fibers, preferably from about 2 to 20% by weight, is sufficient.

The method of mixing the fiber bundles with the components of the bone cement is also important. For example, it has been found that mixing the fiber bundles with liquid monomer prior to combining the polymer powder and liquid results in a congealed mass of damp fibers and it is virtually impossible to mix useful amounts of the damp fibers with the polymer powder. It is presumed that the reason for the clumping of the fibers released from the fiber bundles is due to a large proportion of the liquid monomer being adsorbed to the fiber surfaces, especially after the adhesive binder is dissolved. The adsorbed monomer is then not available during the initial phase of the polymerization process. For example, for a single standard commercially available package of PMMA bone cement containing about 40 grams polymethylmethacrylate polymer and about 20 grams of methylmethacrylate monomer, at a 5% v/v fiber loading with fibers having a diameter of 12 microns, the total surface area of the fibers available to adsorb the liquid monomer is from about 0.5 to 3.0 $m^2$.

Therefore, in accordance with one embodiment of the invention, especially for the addition of smaller volumes of fibers to the bone cement the fiber bundles are pre-mixed with the powdery polymer before mixing with the liquid monomer.

For small amounts of fibers, for example, up to about 5% by volume (v/v), especially up to about 3% v/v, such as 1% or 2% v/v, the fiber bundles may first be mixed with the powdery polymer component. This technique will avoid the clumping problem described above, however, when the liquid monomer is added to the fiber/polymer mixture, the viscosity of the resulting mixture increases very rapidly making the mixture difficult to work, with, especially with more than about 2–3% v/v of fibers. Above about 5%, for example at above 6% v/v, especially at about 8% v/v, it is generally no longer possible to effectively hand mix the liquid monomer with the fiber/polymer mixture. When the resulting mixture is allowed to polymerize small reinforced cement "nuggets," rather than the desired cohesive mass, are formed.

By forming the fibers into bundles the initial available surface area is greatly reduced thereby minimizing the amount of adsorbed liquid monomer unavailable for polymerization. This advantage, however, is offset for larger volumes of the added fiber bundles, e.g. above about 2–4% v/v, especially above 5% v/v, particularly for fibers with smaller diameters, e.g. below about 15–20 microns. For larger diameter fibers, e.g. at least 20 microns, especially at least 30 microns, for example 40 to 100 microns, the total available surface area can be sufficiently reduced to retain the advantage of the fiber bundles, even at higher total fiber volumes, for example, up to 3% v/v or higher, such as up to about 5–8% v/v.

Another useful approach to increase the monomer available for polymerization is to compensate directly for the monomer adsorbed onto the metal fibers by increasing the amount of the monomer relative to the amount of polymer. For example, in standard commercially available acrylic bone cements the polymer powder to monomer liquid ratio, by weight, is 2:1. Increasing the amount of monomer will also increase the time available to mix the fibers and monomer, thereby providing the additional advantage of distributing the fibers more uniformly throughout the cement mass. Still further it is expected that the increased monomer content and increased working time will also lead to an increase in the weight average molecular weight of the resulting polymer. Therefore, in accordance with this embodiment of the invention the bone cement composition is formed by mixing the polymer powder and liquid monomer at a polymer:monomer weight ratio of from 1.5:1 to 1:1.5, for example, about 1.1:1, 1:1 or 1:1.1.

According to still another embodiment of the invention the mixing and handling properties of the reinforced bone cement is facilitated using a low viscosity bone cement (LVC), such as that commercially available from Zimmer, Inc. of Warsaw, Ind. Generally, the LVC exhibit low viscosity (e.g. from about 10 to 1000 cps) due to the smaller size of the finely divided polymer powder, as compared to the viscosities of from about 1000 to 4000 cps for more conventional acrylic or PMMA bone cements. The use of LVC type bone cements will increase the uniformity of fiber distribution by increasing the available mixing time as well as degree of mixing.

By increasing the monomer content and/or by using a low viscosity bone cement it is possible to uniformly incorporate higher total volumes of the reinforcing fibers, for example, from 3 to 10% v/v, especially 3 to 8% v/v.

However, after extensive trial and error experimentation it has been found that the most efficient approach and preferred method of introducing the fibers into the bone cement, especially for fiber amounts above about 2% v/v, is to first mix the powder and liquid monomer components of the bone cement, without the fiber bundles, as in conventional practice for non-reinforced bone cement. After the powdery or granular polymer component is dissolved in the liquid monomer and polymerization has begun (for example, about 30 to 60 seconds, e.g. about 45 seconds, after mixing is completed) the fiber bundles are gradually added to the initial dissolved polymer mixture over a period of from about 15 to 45 seconds, such as 30 seconds. After all the fiber bundles are added to the dissolved polymer mixture, hand mixing is continued for an additional period of time to assure homogeneity. Additional hand mixing for from about 15 to 60 seconds, such as 20, 30, 40 or 45 seconds, is generally sufficient to achieve uniform fiber distribution. The resulting mass may then be centrifuged or subjected to a vacuum according to common current practice, usually after being fed into a cement gun. Centrifuging or vacuum application is used to remove air bubbles or voids present in the cement mass. The cement mass, with or without the air removal, is ready for injection into the body and/or onto the prosthesis.

In order to delay the onset of polymerization after the initial mixing of polymer powder and, liquid monomer and thereby increase available mixing time, it is preferred to chill the liquid monomer before mixing it with the polymer powder. Chilling for about 15 minutes or more in an ice water bath is usually sufficient to slow the polymerization rate to allow the polymer and liquid monomer to be mixed by hand until a substantially homogeneous viscous liquid is formed; usually mixing by hand for about 45 second accomplishes this result.

The invention will now be described by the following illustrative non-limiting examples.

Figure 2:
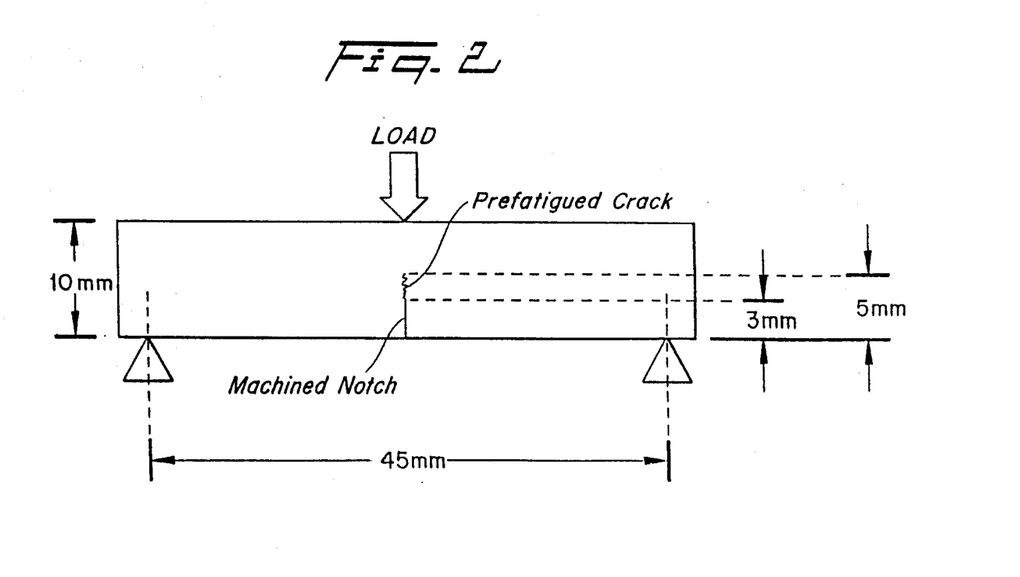
FIG. 2 is a schematic of a 3 point bending, fracture toughness specimen.

In the examples, a three point bend geometry is used for the fracture toughness ($K_{Ic}$) testing. Since there are no ASTM standards for the fracture toughness testing of polymers, a geometry was adapted from ASTM-E 399-83, the standard for fracture toughness testing of metals. However, PMMA acts as a brittle material during rapid fracture, and does not form a large plastic zone, therefore, the specimen dimensions dictated for metals should provide a valid measure of $K_{Ic}$ for PMMA. The specimen geometry is schematically illustrated in FIG. 2. A starter notch is machined with a diamond saw, and then a groove is cut into the tip of the notch with a scalpel. A fatigue crack is grown from the starter notch in order to create a sharp crack in the specimen prior to the $K_{Ic}$ testing. The specimens are prefatigued under load controlled fatigue using an Instron 1125 screw-type testing machine or under stroke controlled fatigue using an Instron 1331 servo-hydraulic testing machine. The latter is considered to enable more stable fatigue crack growth and, therefore, provide more consistent tests.

EXAMPLE 1

A series of fracture toughness tests were performed using commercially available Howmedica Simplex P PMMA bone cement with no fibers (control), 1% by volume (Run A), 2% by volume (Run B), 5% by volume (Run C) or 10% by volume (Run D) of titanium fibers.

The titanium fibers are provided as flat rectangular bundles (obtained from N. V. Bekaert S. A., Zwenegen, Belgium) approximately 0.9 mm high, and 0.3 mm in depth containing several hundred individual Ti fibers, with the fibers in each bundle being either 1.5 mm or 5.0 mm in length and 12 microns in diameter, the fibers in each bundle being glued together by a poly(isobutylmethacrylate) glue.

The Ti fibers have a rough surface which contributes to the adhesion between the Ti reinforcing fibers and the PMMA bone cement.

In this example, the fiber bundles are first added to the polymethylmethacrylate polymer powder component by simply mixing (e.g. "folding") the bundles into the polymer powder with a flat spatula. The liquid methacrylate monomer is similarly mixed with the polymer/fiber premixture for about 60 seconds For Run C the viscosity became very high and mixing of the resulting monomer/polymer/fiber mixture was extremely difficult. For Run D test specimens could not be produced since the reinforced cement polymerized into small "nuggets" rather than a cohesive mass, presumably due to the excessive adsorption of liquid monomer to the fiber surfaces, and the unavailability of the adsorbed monomer for the early portion of the polymerization process.

Each of the control and reinforced bone cements of Runs A, B and C for each of the 1.5 and 5.0 mm Ti fibers were injected using a standard cement gun into Teflon and UHMWPE molds into the shape illustrated in FIG. 2. Prior to molding, the control ("control" refers to specimens made without fibers, i.e. pure bone cement specimens) composition and the compositions of Runs A and B were centrifuged for one minute at 2500 rpm (Damon model HN-SII IEC #204 rotor with a rotating radius of 9.2 cm) to reduce the porosity inherent in bone cement. The composition of Run C was not centrifuged, however, since it has been reported in the literature that standard fracture toughness tests do not reflect the improvements in PMMA due to centrifugation. ("Standard" fracture toughness tests are designed to force a crack to propagate from a predetermined point in a specific direction. The size of crack tip plastic zones in PMMA, the extent of influence of an inclusion on the stress field of a body, the statistics of distribution of inclusions, and the velocity of propagating cracks in mode I fracture toughness tests make it highly unlikely that the inclusions will affect the tendency for the crack to propagate in standard tests.

Figure 7:
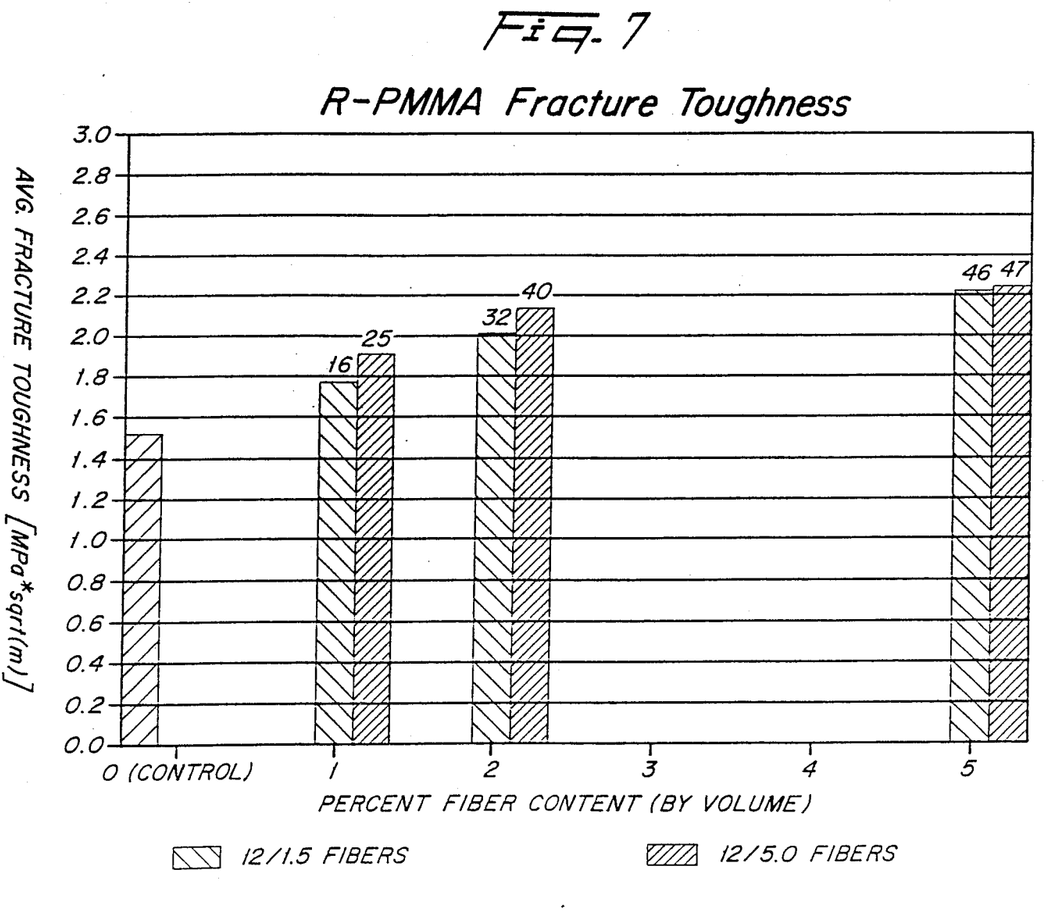
FIG. 7 is a bar graph plotting the average fracture toughness of reinforced acrylic bone cements according to the invention as a function of fiber length and content for 12 micron diameter reinforcing titanium fibers and for a non-reinforced control.

The fracture toughness data for the control and reinforced PMMA specimens are plotted in FIG. 7. There is an increase in fracture toughness with increased fiber content. The number over each bar is the percentage increase in fracture toughness relative to the fracture toughness of the control for the respective sample. At 5% vol. fiber content, the fracture toughness of the 1.5/12 and the 5.0/12 specimens are nearly equal. The increase in fracture toughness for the 5% specimens is nearly 50%, yet it seems that it should be even greater when extrapolated from the 1 to 2% data. It is presumed that amount of monomer adsorbed into the (5%) fiber surfaces was excessive, and the reinforced PMMA did not polymerize as completely as it did for the 1 or 2% specimens.

The fatigue data collected during the prefatiguing of the fracture toughness specimens provides an indication of the fatigue performance of the reinforced PMMA. Although not providing quantitative fatigue data, since starter notches may be of different lengths, such that initial stress intensities may differ from specimen to specimen, and the fatigue cracks may grow to slightly different lengths, the data, nevertheless, is useful to demonstrate some trends. Contrasting the plain PMMA fatigued in stroke control with the 5% reinforced PMMA (of both fiber diameters) shows that the plain PMMA is loaded cyclically with a peak amplitude of approximately 30 lbs. and requires, on the average, approximately 4600 cycles to grow a fatigue crack to an acceptable size. The 1.5 mm Ti fiber reinforced PMMA is loaded with a peak amplitude of 35 lbs., and requires, on the average, 8800 cycles. Thus, the addition of the reinforcing fibers decreases the crack velocity during the crack propagation phase of fatigue.

Load data were also recorded as a function of time during the stroke cycle for the control and for reinforced PMMA specimens. The load distinctly decreases as a crack propagates through the control specimen, since the specimen compliance increases and the displacement remains constant as the crack grows. The load trace for the reinforced PMMA, conversely, remains nearly constant as the crack grows, indicating that the reinforced PMMA specimen is able to maintain its compliance, and carry a significant load. The ability of the reinforced PMMA specimen to maintain a constant load as a crack propagates represents a significant improvement in the fatigue properties over plain PMMA.

EXAMPLE 2

In this example, isobutylmethacrylate bonded Ti fiber bundles prepared from rough surface Ti fibers 22 microns in diameter and 1.5 microns in length were used to reinforce Howmedica Simplex P PMMA surgical bone cement.

Figure 8:
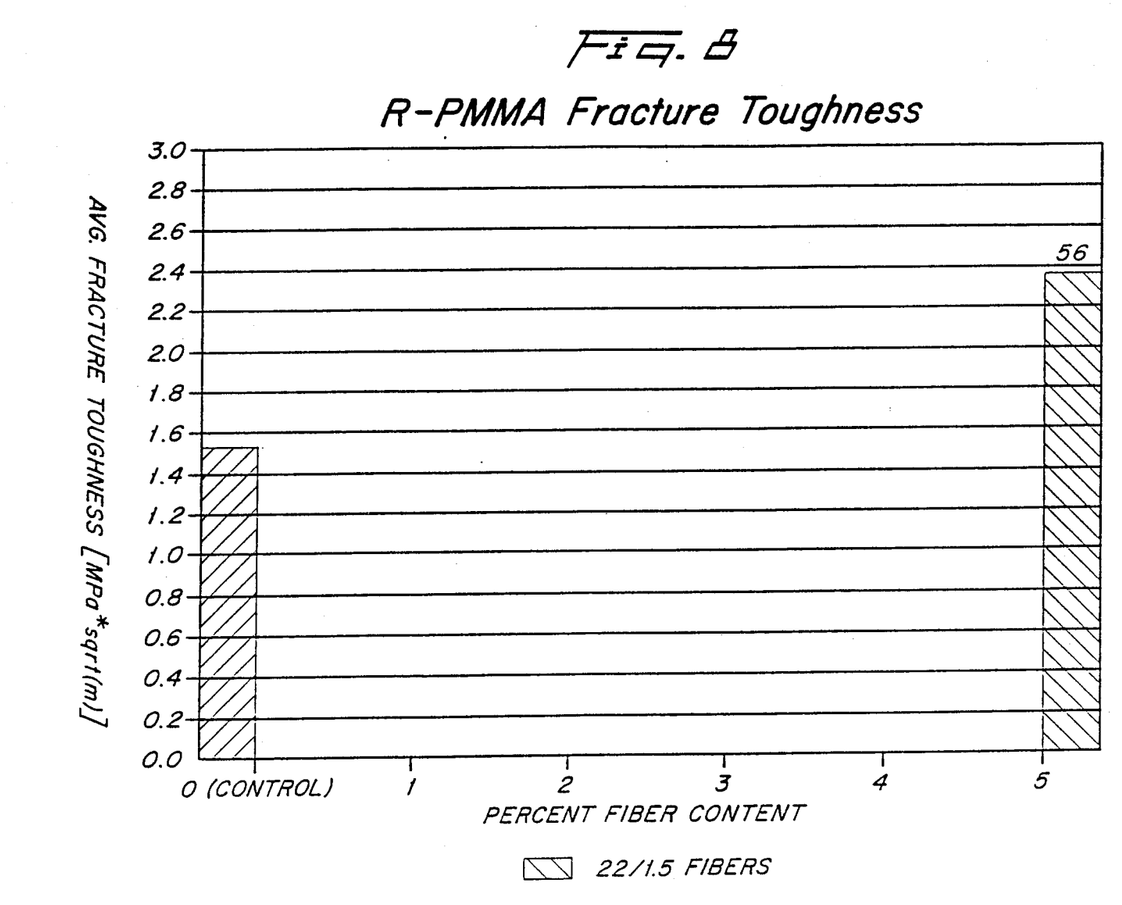
FIG. 8 is a bar graph plotting the average fracture toughness of reinforced acrylic bone cement according to the invention as a function of fiber content for 22 micron diameter titanium fibers and a non-reinforced control.
Figure 10:
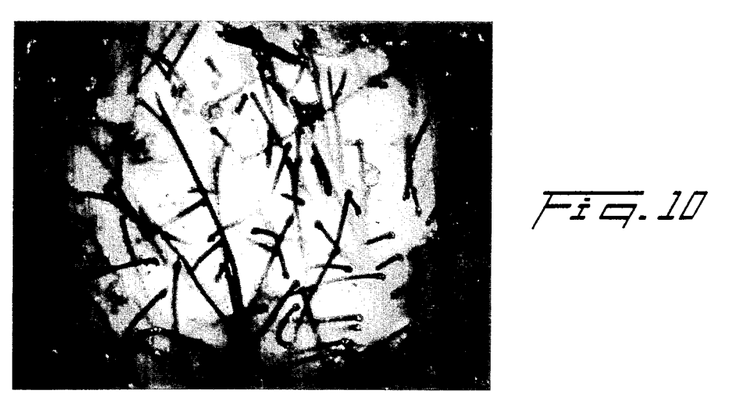
FIGS. 10 and 11 are each microphotographs (magnification 75X) of cross-sections of the cured reinforced bone cement sample obtained according to Example 1, illuminated from both above and below the sample or from only below the sample, respectively.
Figure 11:
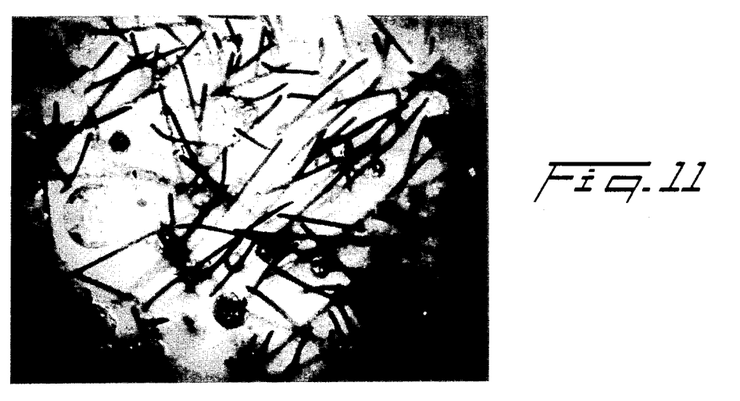

The polymer powder and liquid monomer (cooled in an ice bath for 25 minutes prior to use) are combined, and the mixture is stirred, by hand, for 45 seconds until the mixture becomes a viscous liquid. The Ti fiber bundles are added gradually during the next 30 seconds until 5% by volume is incorporated into the viscous mixture and mixing is continued for an additional 30 seconds. The resulting mixture is transferred to a cement gun and is then injected into molds to form specimens for fracture toughness tests. The results are shown in bar graph form in FIG. 8. There was a 56% increase in toughness as compared to the control versus a 46% increase in toughness for the reinforced PMMA of Run C of Example 1 (Ti fibers=12 microns, 1.5 mm length; 5% v/v). FIG. 10 is a microphotograph (75X) of a cross section of the cured sample illuminated from above and below such that the random distribution of fiber orientation of the fiber strands (seen as dark lines) embedded in the cured cement (seen as a grayish background) can be observed and also illuminated from above such that the fiber cross sections can also be observed (as white dots at the ends of the fibers). FIG. 11 is a similar microphotograph but taken with lighting only from below such that fiber cross sections are not illuminated.

EXAMPLE 3

Figure 9:
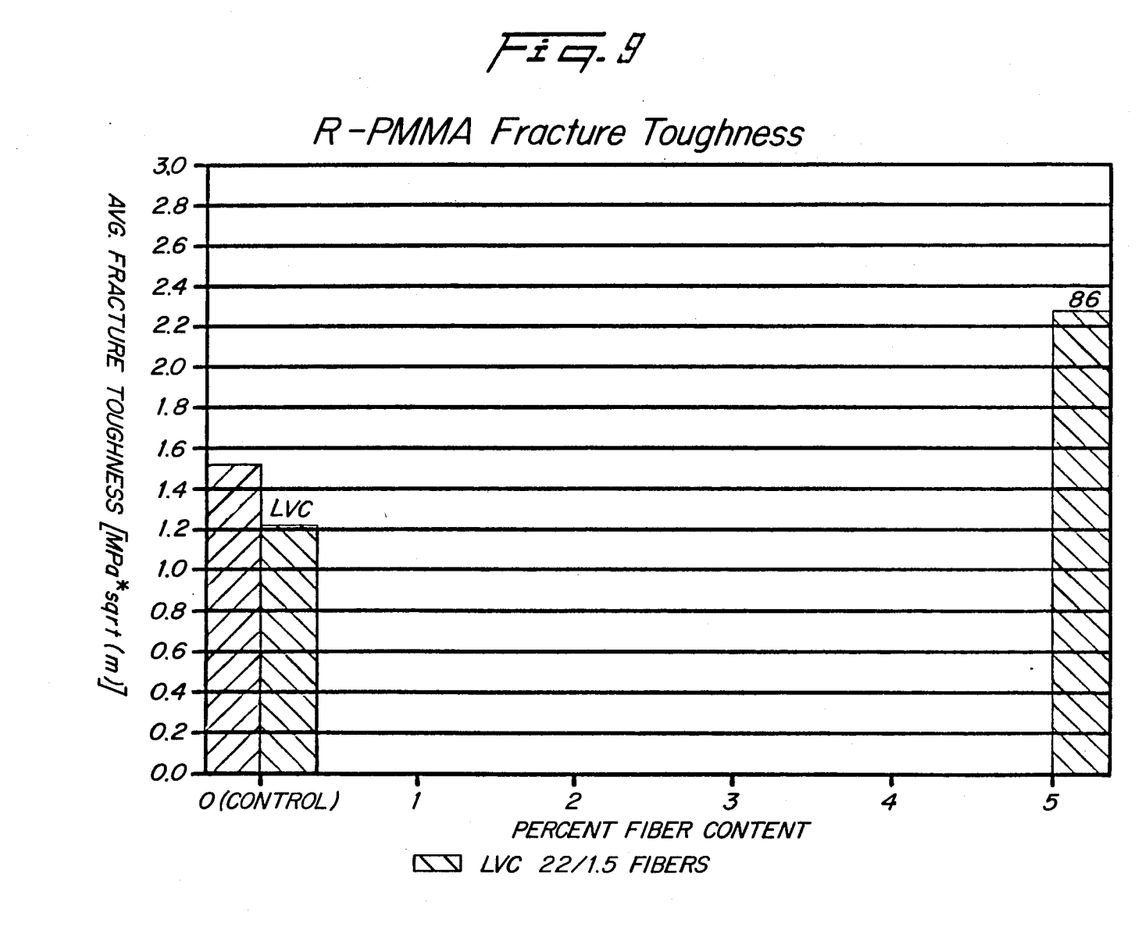
FIG. 9 is a graph plotting the average fracture toughness of reinforced low viscosity acrylic bone cement according to the invention for 22 micron diameter titanium fibers and non-reinforced control.
Figure 12:
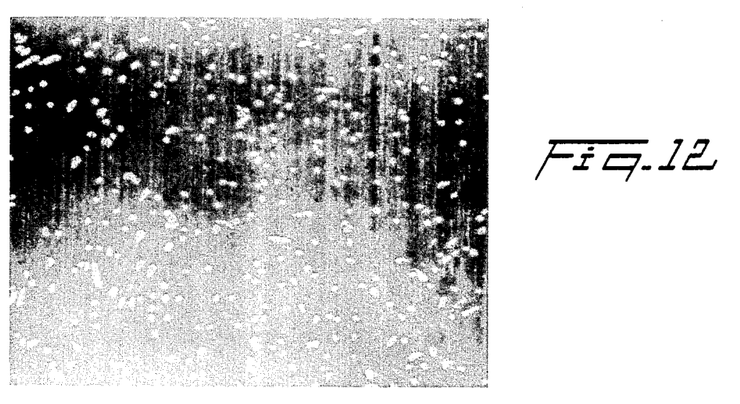
FIG. 12 is a microphotograph (magnification 75X) of a cross-section of the cured reinforced bone cement sample obtained according to Example 2, illuminated from above the sample, and showing the fiber cross sections as white dots.

The procedure of Example 2 was repeated except that in place of the Howmedica Simplex P surgical bone cement Zimmer's LVC surgical bone cement was used. The fracture toughness was 86% greater than the control (Example 1) and 50% greater than the control of Example 2 (see the bar graph plot in FIG. 9). FIG. 12 is a microphotograph (75X) with lighting from above to illuminate fiber cross sections (seen as white dots on the grayish cement background). It is seen from the photograph that the fiber dispersion is fairly uniform, without clumps of fibers, and without large sections where fibers are absent.

What is claimed:

1. A fiber reinforcing material for incorporation into a two component bone cement including particulate polymer component and a polymerizable liquid monomer component and which reinforcing material can be readily incorporated by manual mixing into the bone cement by a surgeon during a surgical operation, said reinforcing material comprising a bundle of reinforcing fibers held together by an adhesive material which is soluble in the liquid monomer component of the two component bone cement, the fibers of said bundle having a diameter in the range of from about 5 to about 100 microns and a length in the range of from about 0.5 to about 10 millimeters, and the length-to-diameter ratio of said bundle being in the range of from about 10:1 to about 1:10.

2. The fiber reinforcing material of claim 1 wherein the reinforcing fibers comprise metallic fibers.

3. The fiber reinforcing material of claim 2 wherein the metal fibers comprise titanium fibers.

4. The fiber reinforcing material of claim 1 wherein the adhesive material comprises an acrylic adhesive.

5. The fiber reinforcing material of claim 4 wherein the acrylic adhesive comprises an acrylate or methacrylate adhesive.

6. The fiber reinforcing material of claim 1 wherein the reinforcing fibers have a diameter of from about 10 to about 80 microns and a length of from about 1 to about 8 millimeters.

7. The fiber reinforcing material of claim 1 which comprises from about 50 to about 500 fibers per bundle.

8. The fiber reinforcing material of claim 1 which comprises from about 100 to about 300 fibers per bundle.

9. The fiber reinforcing material of claim 1 wherein the length-to-diameter ratio is from about 3:1 to about 1:3.

10. A bone cement treatment kit for bone repair or other treatment of a bone defect, said kit comprising (1) finely divided acrylic polymer and (2) polymerizable liquid acrylic monomer for preparation of bone cement useful in bone repair or other bone treatment, and (3) a reinforcing material comprising bundles of reinforcing fibers wherein the fibers of said bundles are bonded to each other by an adhesive material which is soluble in said liquid monomer (2), whereby when said components (1), (2) and (3) are combined the adhesive material dissolves in said liquid monomer and allows said fibers to be homogeneously distributed throughout said bone cement by manual mixing.

11. The kit of claim 10 wherein said fibers are comprised of metal and have a diameter in the range of from about 10 to about 100 microns and a length in the range of from about 0.5 to about 10 millimeters.

12. The kit of claim 11 wherein the metal reinforcing fibers comprise titanium fibers.

13. The kit of claim 12 wherein said bundles of reinforcing fibers have a length-to-diameter ratio of from about 1 to about 1:10.

14. The kit of claim 10 wherein said bundles of reinforcing fibers have a length-to-diameter ratio of from about 1 to about 1:10.

15. The kit of claim 10 wherein said prepolymer (1) comprises a methacrylate or acrylate polymer, said liquid monomer (2) comprises a polymerizable acrylate, methacrylate or methylmethacrylate monomer, and the adhesive material (3) comprises an acrylate or methacrylate based adhesive.

16. The kit of claim 10 wherein each of components (1), (2) and (3) are separately packaged.

17. The kit of claim 10 wherein components (1) and (3) are premixed and component (2) is packaged separately.

18. The kit of claim 16 wherein said package containing said prepolymer (1) further comprises a polymerization initiator.

19. A method for forming a fiber reinforced bone cement for bone repair or other treatment of bone, said method comprising first mixing a powdery polymer component of said bone cement and a plurality of reinforcing fiber bundles, each of said bundles comprising a plurality of short reinforcing fibers bonded together by an adhesive material, and thereafter mixing said fiber-polymer mixture with a polymerizable liquid monomer component of said bone cement which can dissolve said adhesive material and thereby promote uniform and homogeneous distribution of said reinforcing fibers throughout said bone cement.

20. The method of claim 19 which further comprises chilling the polymerizable liquid monomer prior to mixing the liquid monomer with said fiber-polymer mixture.

21. The method of claim 19 wherein the amount of fibers mixed with said powdery polymer comprises up to about 5% by volume, based on the total volume of the bone cement.

22. The method of claim 19 wherein said fiber bundles comprise from about 50 to about 500 reinforcing fibers, per bundle, said reinforcing fibers having a diameter of from about 5 to about 100 microns and a length of from about 0.5 to about 10 millimeters, said bundles having a length-to-diameter ratio of from about 10:1 to about 1:10.

23. The method of claim 22 wherein said reinforcing fibers comprise titanium fibers.

24. A method of forming a fiber reinforced bone cement for bone repair or other treatment of bone, said method comprising premixing a powdery or granular polymer component of said bone cement and a liquid polymerizable monomer component of said bone cement which is a solvent for said polymer component to form a viscous liquid mixture, gradually adding to said liquid mixture a plurality of bundles of short reinforcing fibers, the fibers of said bundles being glued together by an adhesive which is soluble in said liquid monomer and stirring the resulting mixture to distribute the fiber bundles throughout the mixture, while allowing the adhesive component to dissolve in said liquid monomer whereby the individual fibers of said fiber bundles are released into and randomly distributed throughout the bone cement.

25. The method of claim 24 wherein the fiber bundles are added in an amount to provide from about 1 to about 10% by volume of the bone cement.

26. The method of claim 24 wherein the fiber bundles are added in an amount to provide from about 3 to about 10% by volume of the bone cement.

27. The method of claim 24 which further comprises chilling the liquid monomer prior to premixing with the powdery polymer.

28. The method of claim 24 wherein said fiber bundles comprise from about 50 to about 500 reinforcing fibers, per bundle, said reinforcing fibers having a diameter of from about 5 to about 100 microns and a length of from about 0.5 to about 10 millimeters, said bundles having a length-to-diameter ratio of from about 10:1 to about 1:10.

29. The method of claim 28 wherein said reinforcing fibers comprise titanium fibers.

* * * * *